United States Patent [19]

Ikegami et al.

[11] Patent Number: 4,820,840
[45] Date of Patent: Apr. 11, 1989

[54] PROCESS FOR PRODUCING FLUORENE COMPOUNDS

[75] Inventors: Seishi Ikegami; Satoshi Nakao, both of Osaka, Japan

[73] Assignee: Appleton Papers Inc., Appleton, Wis.

[21] Appl. No.: 146,874

[22] Filed: Jan. 22, 1988

Related U.S. Application Data

[63] Continuation-in-part of Ser. No. 84,590, Aug. 11, 1987, abandoned.

[30] Foreign Application Priority Data

Jan. 23, 1987 [JP] Japan ..................... 62-13654

[51] Int. Cl.$^4$ ............... C07D 211/00; C07D 305/14; C07D 401/00; C07F 493/00
[52] U.S. Cl. ..................... 546/15; 549/265; 548/407; 546/187; 546/196; 546/116; 544/350
[58] Field of Search .............. 549/265; 548/407; 546/187, 196, 116, 15; 544/350

[56] References Cited

U.S. PATENT DOCUMENTS 4,658,276  4/1987  Kanda et al. ................. 549/265

FOREIGN PATENT DOCUMENTS

| | | | |
|---|---|---|---|
| 61-022076 | 7/1984 | Japan | 549/265 |
| 60-136553 | 6/1985 | Japan | 549/265 |
| 60-176318 | 8/1985 | Japan | 549/265 |
| 60-189218 | 8/1985 | Japan | 549/265 |
| 60-190439 | 8/1985 | Japan | 549/265 |
| 60-245734 | 10/1985 | Japan | 549/265 |
| 61-124563 | 5/1986 | Japan | 549/265 |

*Primary Examiner*—Mary C. Lee
*Assistant Examiner*—Robert C. Whittenbaugh
*Attorney, Agent, or Firm*—Benjamin Mieliulis

[57] ABSTRACT

An improved process for producing fluorene compounds of the following formula (II) is disclosed:

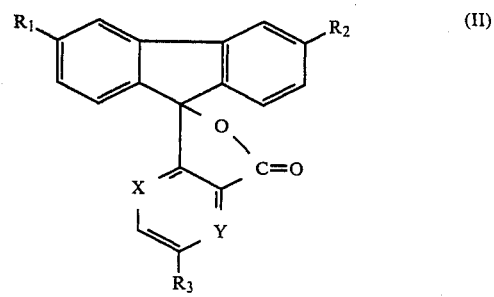

(wherein $R_1$, $R_2$ and $R_3$ are independently a hydrogen atom, an alkylamino group, a dialkylamino group, a pyrrolidino group or a piperdino group; X and Y are independently a carbon atom or a nitrogen atom; and with the proviso that $R_1$ and $R_2$ are not hydrogen atoms simultaneously). The process comprises reacting a lactone compound of the formula (I) (variables being defined as in formula (II))

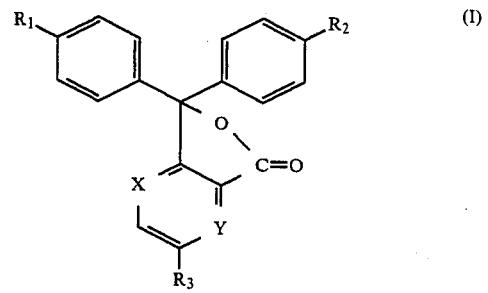

with a mixture of an aluminum halide, a carbonyl compound, and a hydroxy bearing compound.

27 Claims, No Drawings

PROCESS FOR PRODUCING FLUORENE COMPOUNDS

This application is a continuation-in-part of Ser. No. 07/084,590 filed Aug. 11, 1987, now abandoned.

BACKGROUND OF THE INVENTION

1. Field of the Invention

The present invention relates to a process for producing certain fluorene compounds which are useful as electron-donating coloring agents or chromogenic compounds useful in recording systems particularly recording sheets such as heat-sensitive and pressure-sensitive recording sheets.

2. Description of Related Art

Fluorene compounds useful as chromogenic materials are taught in commonly assigned Japan patent application No. 58-074102 filed Apr. 28, 1983. Continued interest in these compounds is evidenced by the continued research related to these types of compounds (for example recent U.S. Pat. No. 4,658,276) and improvements of processes for their preparation (Japan Kokai No. 61-022076).

In the process for producing a fluorene compound represented by the general formula (II), wherein a lactone compound represented by the general formula (I) is subjected to intramolecular ring closure with a mixture of an anhydrous aluminum halide and a carbonyl compound, generally about 20 hours are required for reaction with some attendant dealkylation noted reducing the quality of the product obtained. In the preferred embodiment herein it was surprisingly found that with addition of a compound having at least one hydroxyl group to the mixture of an anhydrous aluminum halide and a carbonyl compound additional advantages of drastic shortening of reaction time and substantial reduction of dealkylation were obtained.

SUMMARY OF THE INVENTION

The present invention relates to an improved process for producing a fluorene compound represented by the general formula (II) comprising subjecting a lactone compound represented by the general formula (I) to reaction with a mixture of an anhydrous aluminum halide and a carbonyl compound, the process being characterized in that a compound having at least one hydroxyl group is further added to the reaction:

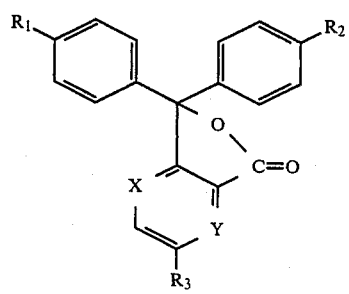

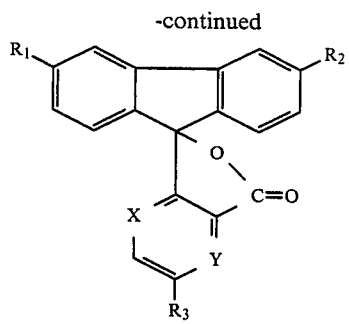

(wherein $R_1$, $R_2$ and $R_3$ are independently a hydrogen atom, an alkylamino group, a dialkylamino group, a pyrrolidino group or a piperidino group; X and Y are independently a carbon atom or a nitrogen atom; and $R_1$ and $R_2$ are not hydrogen atoms simultaneously).

DETAILED DESCRIPTION

The present invention teaches a novel process for producing a fluorene compound which is useful as an electron-donating coloring agent used in pressure-sensitive recording sheets and heat-sensitive recording sheets. More particularly, the present invention teaches to a novel process for producing a fluorene compound represented by the general formula (II) comprising subjecting a lactone compound represented by the general formula (I) to reaction with a mixture of an anhydrous aluminum halide and a carbonyl compound, the process being characterized in that a compound having at least one hydroxyl group is further added to the reaction:

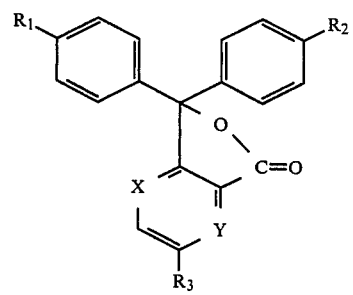

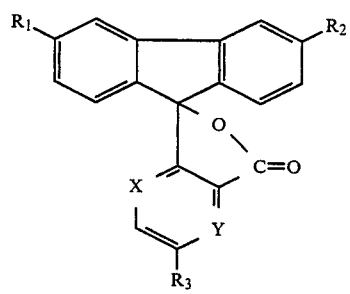

(wherein $R_1$, $R_2$ and $R_3$ independently a hydrogen atom, an alkylamino group, a dialkylamino group, a pyrrolidino group or a piperidino group; X and Y are independently a carbon atom or a nitrogen atom; and $R_1$ and $R_2$ are not hydrogen atoms simultaneously).

Fluorene compounds represented by the general formula (II) are themselves colorless or light-colored crystals. But, in reacting with an acidic substance, they develop a brown, greenish blue or green color and this color image absorbs near infrared rays of 700 to 1000 nm. Therefore, pressure-sensitive or heat-sensitive recording sheets using a fluorene compound represented by the general formula (II) as an electron-donating coloring agent enable optical character recognition using near infrared rays.

Anhydrous aluminum chloride and/or anhydrous aluminum bromide can be used as the anhydrous aluminum halide. It is preferable that the aluminum halide be used in amounts of at least 10 moles per mole of the lactone compound. The use of lesser amounts would lead for difficulty of stirring of the reaction mixture on account of increase in viscosity. The amount has no upper limit but 20 to 30 moles are preferred from the cost standpoint.

As for the carbonyl compound, urea derivatives, amides, carboxylic acids, alkali metal carboxylates can be used. Especially, urea, N-methylpyrrolidone, formamide, dimethylformamide, sodium formate and sodium acetate are preferred. These carbonyl compunds can be used singly or in a mixture of at least two. The amount used is 0.1 to 0.5 mole per mole of the aluminum halide.

Water, inorganic salt hydrates, organic carboxylic acids or metal hydroxides can be used as the compound having at least one hydroxyl group. These compounds can be used singly or in a mixture of at least two.

Any inorganic salt hydrate can be used as the compound having at least one hydroxyl group provided that it does not adversely affect the reaction, however, aluminum halide hydrates such as aluminum chloride hydrate and aluminum bromide hydrate are preferably used. As the organic carboxylic acid, aliphatic carboxylic acids such as formic acid or acetic acid are advantageously usable from a standpoint of prices. As for the metal hydroxide, there can be used magnesium hydroxide, aluminum hydroxide, calcium hydroxide, hydroxides of iron or hydroxides of copper. However, the organic carboxylic acid and the metal hydroxide are not limited to the exemplified above, but any compound can be used provided that it does not adversely affect the reaction.

The amount used of the compound having at least one hydroxyl group depends upon the individual compounds used. When the compound is water, the amount used is 1/150 to ½ mole, preferably 1/60 to ⅓ mole per mole of the anhydrous aluminum halide. When the compound is inorganic salt hydrate, it is used in amount of 1/150 to ½ mole, preferably 1/60 to ⅓ mole in terms of moles of water of hydrate per mole of the anhydrous aluminum halide. When the compound is organic carboxylic acid, it is used in amount of 1/150 to 1 mole, preferably 1/60 to ½ mole in terms of moles of carboxyl group of the organic carboxylic acid per mole of the anhydrous aluminum halide. When the compound is metal hydroxide, it is used in amount of 1/150 to 1 mole, preferably 1/60 to ½ mole in terms of moles of hydroxyl group of the metal hydroxide per mole of the anhydrous aluminum halide. When the amount of the compound used is smaller that the lower limit, no substantial effect is seen to result from the addition. On the other hand, when the amount of the compound used is more than the upper limit, the yield of the product tends to decrease.

The reaction temperature is 70° to 200° C., preferably 90° to 150° C. Since a certain amount of a leuco compound is formed in this reaction, it is preferred that oxygen or air be appropriately introduced into the reaction system during the reaction or that the reaction mixture be subjected to an oxidation treatment after the reaction.

The present invention is explained in more detail below by way of Examples, though the present invention should not be construed as restricted in scope to only these Examples.

EXAMPLE 1

Production of 3,6-bis(dimethylamino)fluorenespiro(9,3')-6'-dimethylaminophthalide 104 parts of 3,3-bis(p-dimethylaminophenyl)-6-dimethylaminophthalide was added to a molten mixture consisting of 1000 parts of anhydrous aluminum chloride, 150 parts of urea and 15 parts of aluminum chloride hexahydrate. The resulting mixture was subjected to reaction for 5 hours at 140° to 145° C. The reaction mixture was placed in 10000 parts of ice water. Thereto was added 24.3 parts of 35% hydrogen peroxide, and the mixture was stirred for 1 hour. The precipitate was collected by filtration and subjected to extraction with 2000 parts of hot toluene. The toluene solution was washed with an aqueous dilute NaOH solution and hot water in that order. To the resulting toluene solution was added 10 parts of active carbon, and the mixture was refluxed with heating. Then, filtration was conducted and the filtrate was subjected to distillation to remove 1500 parts of toluene. The residue was cooled and filtered to obtain 85 parts (theoretical yield: 82.1%) of 3,6-bis(dimethylamino)-fluorenespiro(9,3')-6'-dimethylaminophthalide having a melting point of 240° to 245° C.

EXAMPLE 2

Production of 3,6-bis(dimethylamino)fluorenespiro-(9,3')-6'-dimethylaminophthalide 104 parts of 3,3-bis(p-dimethylaminophenyl)-6-dimethylaminophthalide was added to a molten mixture consisting of 1000 parts of anhydrous aluminum chloride, 150 parts of urea and 8.8 parts of an aqueous 24% aluminum chloride. The resulting mixture was subjected to reaction for 5 hours at 140° to 145° C. The reaction mixture was subjected to the same procedure as in Example 1 to obtain 83.5 parts (theoretical yield: 80.7%) of 3,6-bis(dimethylamino)fluorenespiro(9,3')-6'-dimethylaminophthalide having a melting point of 240° to 245° C.

EXAMPLE 3

Production of 3,6-bis(dimethylamino)fluorenespiro(9,3')-6'-dimethylaminophthalide 104 parts of 3,3-bis(p-dimethylaminophenyl)-6-dimethylaminophthalide was added to a molten mixture consisting of 1000 parts of anhydrous aluminum chloride, 150 parts of urea and 5 parts of water. The resulting mixture was subjected to reaction for 5 hours at 140° to 145° C. The reaction mixture was subjected to the same procedure as in Example 1 to obtain 82.0 parts (theoretical yield: 79.2%) of 3,6-bis(dimethylamino)-fluorenespiro(9,3')-6'-dimethylaminophthalide having a melting point of 240° to 245° C.

EXAMPLE 4

Production of 3,6-bis(dimethylamino)fluorenespiro(9,3')-6'-dimethylaminophthalide 104 parts of 3,3-bis(p-dimethylaminophenyl)-6-dimethylaminophthalide was added to a molten mixture consisting of 950 parts of anhydrous aluminum chloride, 150 parts of urea and 50 parts of aluminum hydroxide.

The resulting mixture was subjected to reaction for 9 hours at 140° to 145° C. The reaction mixture was subjected to the same procedure as in Example 1 to obtain 82.9 parts (theoretical yield: 80.1%) of 3,6-bis(dimethylamino)fluorenespiro(9,3')-6'-dimethylaminophthalide having a melting point of 240° to 245° C.

EXAMPLE 5

Production of 3,6-bis(dimethylamino)fluorenespiro(9,3')-6'-dimethylaminophthalide 104 parts of 3,3-bis(p-dimethylaminophenyl)-6-dimethylaminophthalide was added to a molten mixture consisting of 1000 parts of anhydrous aluminum chloride, 150 parts of urea and 30 parts of acetic acid. The resulting mixture was subjected to reaction for 4 hours at 140° to 145° C. The reaction mixture was subjected to the same procedure as in Example 1 to obtain 83.7 parts (theoretical yield: 80.9%) of 3,6-bis(dimethylamino)fluorenespiro(9,3')-6'-dimethylaminophthalide having a melting point of 240° C. to 245° C.

COMPARATIVE EXAMPLE

Production of 3,6-bis(dimethylamino)-fluorenespiro(9,3')-6'-dimethylaminophthalide 104 parts of 3,3-bis(p-dimethylaminophenyl)-6-dimethylaminophthalide was added to a molten mixture consisting of 1000 parts of anhydrous aluminum chloride and 150 parts of urea. The resulting mixture was subjected to reaction for 24 hours at 140° to 145° C. The reaction mixture was subjected to the same procedure as in Example 1 to obtain 84.3 parts (theoretical yield: 81.4%) of 3,6-bis(dimethylamino)fluorenespiro(9,3')-6'-dimethylaminophthalide having a melting point of 235° to 240° C.

obtain 68.3 parts (theoretical yield: 66.0%) of 3,6-bis(dimethylamino)fluorenespiro(9,3')-6'-dimethylaminophthalide having a melting point of 240° to 245° C.

EXAMPLE 7

Production of 3-dimethylamino-6-diethylaminofluorenespiro(9,3')-6'-dimethylaminophthalide 120 parts of 3-p-dimethylaminophenyl-3-p-diethylaminophenyl-6-dimethylaminophthalide was added to a molten mixture consisting of 800 parts of anhydrous aluminum chloride, 120 parts of urea and 12 parts of aluminum chloride hexahydrate. The resulting mixture was subjected to reaction for 6 hours at 140° to 145° C. The reaction mixture was subjected to the same procedure as in Example 1 to obtain 77.2 parts (theoretical yield: 64.8%) of 3-dimethylamino-6-diethylaminofluorenespiro(9,3')-6'-dimethylaminophthalide having a melting point of 230° to 235° C.

EXAMPLE 8

Production of 3,6-bis(diethylamino)fluorenespiro(9,3')-6'-diethylaminophthalide 104 parts of 3,3-bis(p-diethylaminophenyl)-6-diethylaminophthalide was added to a molten mixture consisting of 750 parts of anhydrous aluminum chloride, 112.5 parts of urea and 12 parts of aluminum chloride hexahydrate. The resulting mixture was subjected to reaction for 7 hours at 140° to 145° C. The reaction mixture was subjected to the same procedure as in Example 1 to obtain 65 parts (theoretical yield: 62.7%) of 3,6-bis(diethylamino)fluorenespiro(9,3')-6'-diethylaminophthalide having a melting point of 205° to 210° C.

TABLE 1

| | Production of 3, 6-bis(dimethylamino) fluorenespiro (9, 3')-6'-dimethylaminophthalide | | | | |
|---|---|---|---|---|---|
| | Hydroxyl group-containing compound | Reaction time (hr) | Theoretical yield (%) | Melting point (°C.) | Content of dealkylation product (%) (Measured by TLC scanner) |
| Example 1 | Aluminium chloride hexahydrate | 5 | 82.1 | 240 to 245 | 3.1 |
| Example 2 | Aqueous 24% aluminum chloride solution | 5 | 80.7 | 240 to 245 | 3.0 |
| Example 3 | Water | 5 | 79.2 | 240 to 245 | 3.4 |
| Example 4 | Aluminum hydroxide | 9 | 80.1 | 240 to 245 | 4.9 |
| Example 5 | Acetic Acid | 4 | 80.9 | 240 to 245 | 4.2 |
| Comparative Example | — | 24 | 81.4 | 235 to 240 | 12.4 |

The results of Examples 1 to 5 and Comparative Example are summarized in Table 1.

EXAMPLE 6

Production of 3,6-bis(dimethylamino)fluorenespiro(9,3')-6'-dimethylaminophthalide 104 parts of 3,3-bis(p-dimethylaminophenyl)-6-dimethylaminophthalide was added to a molten mixture consisting of 500 parts of anhydrous aluminum chloride 75 parts of urea and 15 parts of aluminum chloride hexohydrate. The resulting mixture was subjected to reaction for 7 hours at 140° to 145° C. The reaction mixture was subjected to the same procedure as in Example 1 to

EXAMPLE 9

Production of 3-dimethylamino-6-dibutylaminofluorenespiro (9,3')-6'-dimethylaminophthalide 125 parts of 3-p-dimethylaminophenyl-3-p-dibutylaminophenyl-6-dimethylaminophthalide was added to a molten mixture consisting of 800 parts of anhydrous aluminum chloride, 120 parts of urea and 36 parts of aluminum chloride hexahydrate. The resulting mixture was subjected to reaction for 4 hours at 135° to 140° C. The reaction mixture was subjected to the same procedure as in Example 1 to obtain 84.6 parts (theoretical yield: 68.0%) of 3-dimethylamino-6-dibutylamino-fluorenespiro(9,3')-6'-dimethylaminophthalide having a melting point of 145° to 150° C.

EXAMPLE 10

Production of 3-dimethylamino-6-pyrrolidino-fluorenespiro (9,3')-6'-dimethylaminophthalide 110 parts of 3-p-dimethylaminophenyl-3-p-pyrrolidinophenyl-6-dimethylaminophthalide was added to a molten mixture consisting of 1000 parts of anhydrous aluminum chloride, 150 parts of urea and 24 parts of aluminum chloride hexahydrate. The resulting mixture was subjected to reaction for 4 hours at 135° to 140° C. The reaction mixture was subjected to the same procedure as in Example 1 to obtain 44.1 parts (theoretical yield: 40.2%) of 3-dimethylamino-6-pyrrolidinofluorenespiro-(9,3')-6'-dimethylaminophthalide having a melting point of 275° to 280° C.

EXAMPLE 11

Production of 3-dimethylamino-6-piperidino-fluorenespiro (9,3')-6'-dimethylaminophthalide 114 parts of 3-p-dimethylaminophenyl-3-p-piperidinophenyl-6-dimethylaminophthalide was added to a molten mixture consisting of 1000 parts of anhydrous aluminum chloride, 150 parts of urea and 24 parts of aluminum chloride hexahydrate. The resulting mixture was subjected to reaction for 4 hours at 135° to 140° C. The reaction mixture was subjected to the same procedure as in Example 1 to obtain 53.5 parts (theoretical yield: 47.1%) of 3-dimethylamino-6-piperidinofluorenespiro-(9,3')-6'-dimethylaminophthalide having a melting point of 225° to 230° C.

EXAMPLE 12

Production of 3,6-bis(dibutylamino)fluorenespiro (9,3')-6'-dimethylaminophthalide 145 parts of 3,3-bis(p-dibutylaminophenyl)-6-dimethylaminophthalide was added to a molten mixture consisting of 1000 parts of anhydrous aluminum chloride, 150 parts of urea and 20 parts of aluminum chloride hexahydrate. The resulting mixture was subjected to reaction for 6 hours at 140° to 145° C. The reaction mixture was subjected to the same procedure as in Example 1 to obtain 3,6-bis(-dibutylamino)-fluorenespiro(9,3')-6'-dimethylaminophthalide having a melting point of 151° to 154° C.

EXAMPLE 13

Production of 3-dibutylamino-6-dimethylamino-fluorenespiro (9,3')-6'-dibutylaminophthalide 145 parts of 3-p-dibutylaminophenyl-3-p-dimethylaminophenyl-6-dibutylaminophthalide was added to a molten mixture consisting of 1000 parts of anhydrous aluminum chloride, 150 parts of urea and 15 parts of aluminum chloride hexahydrate. The resulting mixture was subjected to reaction for 7 hours at 140° to 145° C. The reaction mixture was subjected to the same procedure as in Example 1 to obtain 3-dibutylamino-6-dimethylamino-fluorenespiro(9,3')-6'-dibutylaminophthalide having a melting point of 144° to 147° C.

EXAMPLE 14

Production of 3,6-bis(dibutylamino)fluorenespiro (9,3')-6'-dibutylaminophthalide 165 parts of 3,3-bis(p-dibutylaminophenyl)-6-dibutylaminophthalide was added to a molten mixture consisting of 1000 parts of anhydrous aluminum chloride, 150 parts of urea and 20 parts of aluminum chloride hexahydrate. The resulting mixture was subjected to reaction for 8 hours at 140° to 145° C. The reaction mixture was subjected to the same procedure as in Example 1 to obtain 3,6-bis(-dibutylamino)fluorenespiro(9,3')-6'-dibutylaminophthalide having a melting point of 111° to 113° C.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive variations and changes can be made by those skilled in the art without departing from the spirit and scope of the invention.

What we claim is:

1. A process for the preparation of a fluorene compound represented by the formula (II)

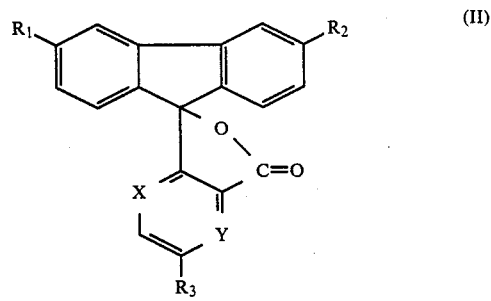

which comprises:
  reacting a lactone compound represented by the formula (I)

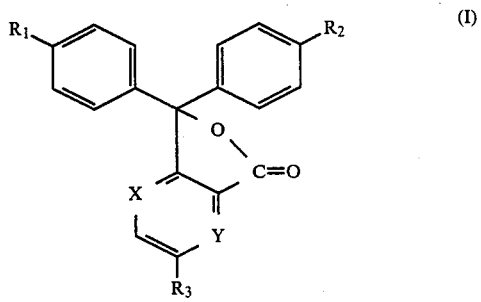

together with a mixture of an aluminum halide, a carbonyl compound selected from the group consisting of urea, N-methylpyrrolidone, formamide, dimethylformamide, sodium formate, sodium acetate an mixtures thereof, and a compound having at least one hydroxyl group, selected from the group consisting of water, inorganic salt hydrates, metal hydroxides and mixtures thereof,
  wherein, in formulas (I) and (II), $R_1$ $R_2$ and $R_3$ are independently selected from hydrogen, alkylamino, dialkylamino, pyrrolidino and piperidino, with the provision that $R_1$ and $R_2$ are not hydrogen simultaneously,
  X and Y are independently carbon or nitrogen.

2. The process according to claim 1, wherein the anhydrous aluminum halide is anhydrous aluminum chloride or anhydrous aluminum bromide.

3. The process according to claim 1, wherein the carbonyl compound is urea.

4. The process according to claim 1, wherein water is used in amount of 1/150 to ½ mole per mole of the anhydrous aluminum halide.

5. The process according to claim 1, wherein the inorganic salt hydrate is used in amount of 1/150 to ½ mole in terms of moles of water of hydrate per mole of the anhydrous aluminum halide.

6. The process according to claim 5, wherein the metal hydroxide is used in amount of 1/150 to 1 mole in terms of moles of hydroxyl group of the metal hydroxide per mole of the anhydrous aluminum halide.

7. The process according to claim 1, wherein the anhydrous aluminum halide is used in amount of at least 10 moles per mole of the lactone compound.

8. The process according to claim 1, wherein the reaction is conducted at 70° to 200° C.

9. The process according to claim 8, wherein the reaction is conducted at 90° to 150° C.

10. The process according to claim 1, wherein the fluorene compound of formula (II) is 3,6-bis(dimethylamino)fluorenespiro(9,3')-6'-dimethylaminophthalide.

11. The process according to claim 1, wherein the fluorene compound of formula (II) is 3-dimethylamino-6-diethylaminofluorenespiro(9,3')-6'-dimethylaminophthalide.

12. The process according to claim 1, wherein the fluorene compound of formula (II) is 3,6-bis(diethylamino)fluorenespiro(9,3')-6'-diethylaminophthalide.

13. The process according to claim 1, wherein the fluorene compound of formula (II) is 3-dimethylamino-6-dibutylaminofluorenespiro(9,3')-6'-dimethylaminophthalide.

14. The process according to claim 1, wherein the fluorene compound of formula (II) is 3-dimethylamino-6-pyrrolidinofluorenespiro(9,3')-6'-dimethylaminophthalide.

15. The process according to claim 1, wherein the fluorene compound of formula (II) is 3-dimethylamino-6-piperidinofluorenespiro(9,3')-6'-dimethylaminophthalide.

16. The process according to claim 1, wherein the fluorene compound of formula (II) is 3,6-bis(dibutylamino)fluorenespiro(9,3')-6'-dimethylaminophthalide.

17. The process according to claim 1, wherein the fluorene compound of formula (II) is 3-dibutylamino-6-dimethylaminofluorenespiro(9,3')-6'-dibutylaminophthalide.

18. The process according to claim 1, wherein the fluorene compound of formula (II) is 3,6-bis(dibutylamino)fluorenespiro(9,3')-6'-dibutylaminophthalide.

19. The process according to claim 10, wherein the lactone compound of formula (I) is 3,3-bis(p-dimethylaminophenyl)-6-dimethylaminophthalide.

20. The process according to claim 11, wherein the lactone compound of formula (I) is 3-p-dimethylaminophenyl-3-p-diethylaminophenyl-6-dimethylaminophthalide.

21. The process according to claim 12, wherein the lactone compound of formula (I) is 3,3-bis(p-diethylaminophenyl)-6-diethylaminophthalide.

22. The process according to claim 13, wherein the lactone compound of formula (I) is 3-p-dimethylaminophenyl-3-p-dibutylaminophenyl-6-dimethylaminophthalide.

23. The process according to claim 14, wherein the lactone compound of formula (I) is 3-p-dimethylaminophenyl-3-p-pyrrolidinophenyl-6-dimethylaminophthalide.

24. The process according to claim 15, wherein the lactone compound of formula (I) is 3-p-dimethylaminophenyl-3-p-piperidinophenyl-6-dimethylaminophthalide.

25. The process according to claim 16, wherein the lactone compound of formula (I) is 3,3-bis(p-dibutylaminophenyl)-6-dimethylaminophthalide.

26. The process according to claim 17, wherein the lactone compound of formula (I) is 3-p-dibutylaminophenyl-3-p-dimethylaminophenyl-6-dibutylaminophthalide.

27. The process according to claim 18, wherein the lactone compound of formula (I) is 3,3-bis(p-dibutylaminophenyl)-6-dibutylaminophthalide.

* * * * *

UNITED STATES PATENT AND TRADEMARK OFFICE
CERTIFICATE OF CORRECTION

PATENT NO. : 4,820,840
DATED : April 11, 1989
INVENTOR(S) : Ikegami and Nakao

It is certified that error appears in the above-identified patent and that said Letters Patent is hereby corrected as shown below:

Title page: the assignee "Appleton Papers Inc., Appleton, Wis." should read -- Yamamoto Chemicals Inc., Osaka Pref., Japan. --

Signed and Sealed this

Thirty-first Day of October, 1989

Attest:

DONALD J. QUIGG

*Attesting Officer*  *Commissioner of Patents and Trademarks*